(12) United States Patent
King et al.

(10) Patent No.: US 7,657,318 B2
(45) Date of Patent: *Feb. 2, 2010

(54) TECHNIQUE FOR ADJUSTING THE LOCUS OF EXCITATION OF ELECTRICALLY EXCITABLE TISSUE

(75) Inventors: Gary W. King, Fridley, MN (US); Robert Leinders, Maaslandstaat (NL); Greg Hrdlicka, Plymouth, MN (US); Michael D. Baudino, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 808 days.

This patent is subject to a terminal disclaimer.

(21) Appl. No.: 11/273,310

(22) Filed: Nov. 14, 2005

(65) Prior Publication Data

US 2006/0079937 A1    Apr. 13, 2006

Related U.S. Application Data

(60) Continuation of application No. 10/247,981, filed on Sep. 20, 2002, now Pat. No. 6,988,006, which is a continuation of application No. 09/523,072, filed on Mar. 10, 2000, now Pat. No. 6,505,078, which is a continuation-in-part of application No. 09/312,470, filed on May 17, 1999, now Pat. No. 6,083,252, which is a division of application No. 08/814,432, filed on Mar. 10, 1997, now Pat. No. 5,925,070, which is a continuation-in-part of application No. 08/637,361, filed on Apr. 25, 1996, now Pat. No. 5,713,922, which is a continuation-in-part of application No. 08/627,578, filed on Apr. 4, 1996, now abandoned.

(51) Int. Cl.
*A61N 1/36* (2006.01)

(52) U.S. Cl. .................................... 607/46

(58) Field of Classification Search .............. 607/66, 607/68, 70, 72, 74, 116–119, 46, 67, 148
See application file for complete search history.

(56) References Cited

U.S. PATENT DOCUMENTS 1,935,138 A    11/1933    Windisch (Continued)

FOREIGN PATENT DOCUMENTS

EP    0 236 513    9/1987
WO    WO 95/19804    7/1995

OTHER PUBLICATIONS

J. Holsheimer, Wilbert A. Wesselink, M.Sc., "Effect of Anode-Cathode Configuration on Paresthesia Coverage in Spinal Cord Stimulation," Institute for Biomedical Technology, Department of Electrical Engineering, Neurosurger, vol. 41, No. 3, pp. 654-660, Sep. (1997).

(Continued)

*Primary Examiner*—George R Evanisko
(74) *Attorney, Agent, or Firm*—Banner & Witcoff, Ltd.

(57) ABSTRACT

The locus of electrically excitable tissue where action potentials are induced can be controlled using the physiological principle of electrotonus. In one embodiment, first and second pulses are applied to first and second electrodes, respectively, to generate first and second subthreshold potential areas, respectively, within the tissue. The locus within the tissue where action potentials are induced is determined by a superposition of the first and second subthreshold areas according to the physiological principle of electrotonus. In another embodiment, a two-dimensional array of electrodes are formed. The cathode may be positioned near the center of the two-dimensional array or may be left out. The first and second subthreshold areas may thereby be steered. An array of anodal rings may be used to contain the field of excitation.

19 Claims, 16 Drawing Sheets

U.S. PATENT DOCUMENTS

| | | |
|---|---|---|
| 3,822,708 A | 7/1974 | Zilber |
| 3,850,161 A | 11/1974 | Liss |
| 3,918,461 A | 11/1975 | Cooper |
| 3,920,024 A | 11/1975 | Bowers |
| 3,957,036 A | 5/1976 | Normann |
| 4,524,774 A | 6/1985 | Hildebrandt |
| 4,543,955 A | 10/1985 | Schroeppel |
| 4,548,203 A | 10/1985 | Tacker, Jr. et al. |
| 4,570,640 A | 2/1986 | Barsa |
| 4,702,254 A | 10/1987 | Zabara |
| 4,750,499 A | 6/1988 | Hoffer |
| 4,867,164 A | 9/1989 | Zabara |
| 4,877,032 A | 10/1989 | Heinze et al. |
| 4,964,411 A | 10/1990 | Johnson et al. |
| 5,002,053 A | 3/1991 | Garcia-Rill et al. |
| 5,018,523 A | 5/1991 | Bach, Jr. et al. |
| 5,025,807 A | 6/1991 | Zabara |
| 5,081,990 A | 1/1992 | Deletis |
| 5,121,754 A | 6/1992 | Mullett |
| 5,167,229 A | 12/1992 | Peckham et al. |
| 5,314,458 A | 5/1994 | Najafi et al. |
| 5,314,495 A | 5/1994 | Kovacs |
| 5,324,309 A | 6/1994 | Kallok |
| 5,332,401 A | 7/1994 | Davey et al. |
| 5,370,665 A | 12/1994 | Hudrlik |
| 5,501,703 A | 3/1996 | Holsheimer et al. |
| 5,507,788 A | 4/1996 | Lieber |
| 5,713,922 A * | 2/1998 | King .............................. 607/2 |
| 5,925,070 A * | 7/1999 | King et al. .................... 607/67 |
| 6,038,480 A | 3/2000 | Hrklicka et al. |
| 6,083,252 A * | 7/2000 | King et al. .................... 607/70 |
| 6,505,078 B1 * | 1/2003 | King et al. .................... 607/67 |
| 6,988,006 B2 * | 1/2006 | King et al. .................... 607/70 |

OTHER PUBLICATIONS

J. Holsheimer, J.J. Strujik, N.R. Ras, "Effects of Electrode Geometry and Combination on Nerve Fibre Selectrivity in Spinal Cord Stimulation," Institute for Biomedical Technology, Medical & Biological Engineering & Comput., vol. 33, pp. 676-682 (1995).

J. Holsheimer, G. Barolat, J.J. Strujik, J. He, "Significance of the Spinal Cord Position in Spinal Cord Stimulation," Institute for Biomedical Technology, Department of Neurological Surgery, Acta Neurochir (1995) [Suppl] 64:119-124.

J. Holsheimer, J.J. Strujik, N.J.M. Rijkhoff, "Contact Combinations in Epidural Spinal Cord Stimulation," Stereotact Funct Neurosurg, vol. 56, pp. 220-233 (1991).

Kirsten E.I. Deurloo, Jan Holsheimer, "Transverse Tripolar Stimulation for Selective FNS," IEEE/EMBS Conference, Amsterdam (1996).

J.J. Strujik, J. Holsheimer, "Transverse Tripolar Spinal Cord Stimulation: Theoretical Performance of a Dual Channel System," Medical & Biological Engineering & Comput., vol. 34, pp. 273-279 (1996).

* cited by examiner (PATTERNS WITH 4 ELECTRODES)

Figure 23
(PATTERNS WITH SIX ELECTRODES)
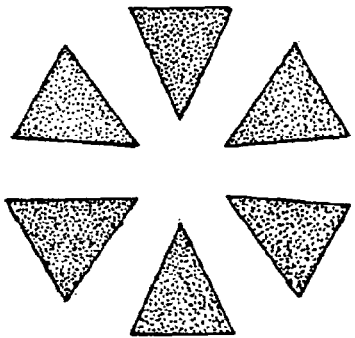
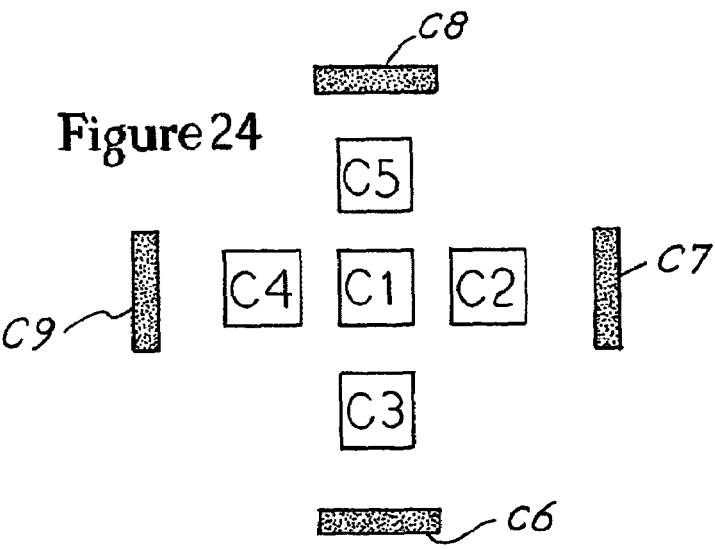
Figure 24
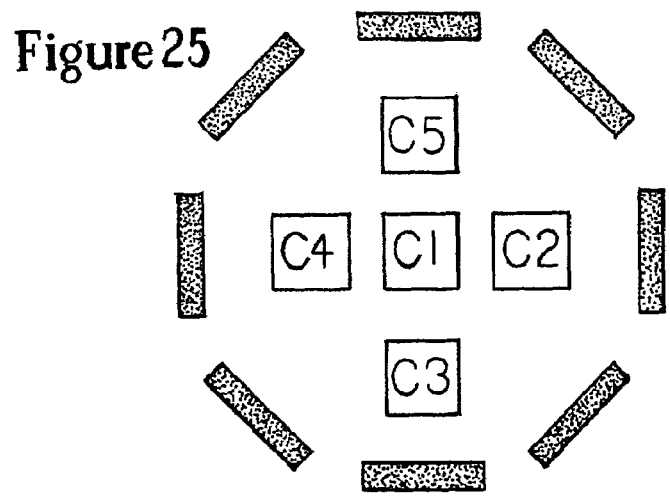
Figure 25

TECHNIQUE FOR ADJUSTING THE LOCUS OF EXCITATION OF ELECTRICALLY EXCITABLE TISSUE

This is a continuation of patent application Ser. No. 10/247,981, filed Sep. 20, 2002, which is a continuation of patent application Ser. No. 09/523,072, filed Mar. 10, 2000, now U.S. Pat. No. 6,505,078, which is a continuation-in-part of patent application Ser. No. 09/312,470, filed on May 17, 1999, now U.S. Pat. No. 6,083,252, which is a divisional of patent application Ser. No. 08/814,432, filed Mar. 10, 1997, now U.S. Pat. No. 5,925,070, which is a continuation-in-part of patent application Ser. No. 08/637,361, filed on Apr. 25, 1996, now U.S. Pat. No. 5,713,922, which is a continuation-in-part of patent application Ser. No. 08/627,578, filed on Apr. 4, 1996, now abandoned, for which priority is claimed. These patents and patent applications are each incorporated herewith by reference in their entireties.

FIELD OF THE INVENTION

This invention relates to means of stimulating electrically excitable tissue, and more particularly relates to means for adjusting the locus at which action potentials are induced in such tissue.

DESCRIPTION OF THE RELATED ART

Two major practical problems reduce the efficacy of epidural spinal cord stimulation (SCS) for pain control. One is the difficulty of directing the stimulation-induced paresthesia to the desired body part and the other is the problem of disagreeable sensations or motor responses to the stimulation, which reduce the comfortable amplitude range of the stimulation. It is generally agreed that in SCS, for chronic pain, paresthesia should cover the whole pain region. With present stimulation methods and equipment, only highly skilled and experienced practitioners are able to position a stimulation lead in such a way that the desired overlap is reached and desired results are obtained over time with minimal side effects. It requires much time and effort to focus the stimulation on the desired body region during surgery and, using pulses with single value cathodes, it is difficult to redirect it afterwards, even though some readjustments can be made by selecting a different contact combination, pulse rate, pulse width or voltage.

Redirecting paresthesia after surgery is highly desirable. Even if paresthesia covers the pain area perfectly during surgery, the required paresthesia pattern often changes later due to lead migration, or histological changes (such as the growth of connective tissue around the stimulation electrode) or disease progression. The problem of lead placement has been addressed by U.S. Pat. No. 5,121,754 by the use of a lead with a deformable distal shape. These problems are not only found with SCS, but also with peripheral nerve stimulation (PNS), depth brain stimulation (DBS), cortical stimulation and also muscle or cardiac stimulation.

The era of precise control of electrical fields for excitation of tissue by use of multiple voltages is disclosed in PCT International Publication No. WO 95/19804 (counterpart to Holsheimer et al., U.S. Pat. No. 5,501,703) (the "Holsheimer references"). The Holsheimer references describe the use of electrodes that are "in-line," namely that they are disposed "symmetrically" along a line. The three juxtaposed electrodes have two simultaneous voltages relative to one of them, each with its own amplitude. This approach allows "steering" of the electric fields created by these electrodes. Particularly, the electrical field pattern is adjusted by varying the electrical field generated between those electrodes along that line. The locus of excitation is correspondingly varied with that variation in the electrical field pattern. For example, if a central electrode of three roughly collinear electrodes is a cathode (−) then the outer anodes push the areas of excitation toward the middle, and shield outer areas from excitation. As the anodal pulses are varied in amplitude, the field steers toward the outside.

However, the Holsheimer references disclose a system that requires three electrodes that are optimally spaced symmetrically along a line. It is a serious handicap during the surgical procedure to place these electrodes in the body. Often, a lead such as a paddle is used for mounting the multiple electrodes in the optimally spaced positions. This lead is then inserted within a patient near the tissue to be excited, and electrical excitation is applied to the lead. Unfortunately, placement of a lead such as the paddle within a patient, can be difficult since the paddle can be surgically difficult to manipulate adjacent the spinal cord. Thus, it would be desirable to be able to adjust the locus of excitation in electrically excitable tissue without the use of optimally spaced electrodes.

In addition, the Holsheimer system is limited in that steering is accomplished over a linear path. It would be desirable to adjust the locus of excitation in electrically excitable tissue over a greater area.

OBJECTS OF THE INVENTION

Accordingly, a primary object of the present invention is to provide a method and apparatus for adjusting the locus of excitation in electrically excitable tissue using electrodes that do not have to be optimally spaced in a line.

In particular, an object of the present invention is to adjust areas of subthreshold excitation in order to adjust an area of superposition of such areas of subthreshold excitation. The area of superposition determines the locus of excitation of electrically excitable tissue.

Another object of the invention is to provide a method and apparatus for adjusting the locus of superthreshold excitation in electrically excitable tissue using electrodes that are spaced in a two dimensional array.

Another object of the invention is to add outer anodes to a grouping of cathodal electrodes to shield areas farther out and to keep activation of tissue nearer to the cathodes.

SUMMARY OF THE INVENTION

In a principle aspect, the present invention takes the form of an apparatus and method for inducing action potentials at an adjustable locus of electrically excitable tissue. In accordance with the invention, a first pulse having a first amplitude and a first pulse width is applied to the tissue via a first electrode adapted to be adjacent said tissue. Similarly, a second pulse having a second amplitude and a second pulse width is applied to the tissue via a second electrode adapted to be adjacent said tissue.

The application of the first pulse generates a first subthreshold potential area in said tissue, and the application of the second pulse generates a second subthreshold potential area. The first subthreshold area is determined by the first amplitude and the first pulse width of the first pulse, and the second subthreshold area is determined by the second amplitude and the second pulse width of the second pulse. A superposition of the first and second subthreshold areas results in a suprathreshold potential area of said adjustable locus where the action potentials are induced.

This embodiment of the present invention may be applied to particular advantage when adjusting the locus where the action potentials are induced. The first amplitude or the first pulse width of the first pulse can be adjusted for a corresponding adjustment of the first subthreshold area and contribute, in turn, to the volume where suprathreshold potentials are produced. Similarly, the second amplitude or the second pulse width of the second pulse can be adjusted for a corresponding adjustment of the second subthreshold area and contribute, in turn, to the volume of where suprathreshold potentials are produced. The size and location of the suprathreshold potential area can thus be controlled.

In another aspect of the present invention, a time delay between the application of the first and second pulses can be varied for a corresponding adjustment in size and location of the suprathreshold potential area. The time delay between the application of the first and second pulses can be measured from the end time of the first pulse to the begin time of the second pulse. Additionally, that delay can be measured as a difference between a first weighted average time of the first pulse and a second weighted average time of the second pulse, or between a first peak time of the first pulse and a second peak time of the second pulse.

In another aspect of the invention, simultaneous pulses of varying amplitudes are delivered to multiple electrodes (cathodes), which are arranged in a two-dimensional array. As a cross-pattern, there may be a central electrode at the center of the pattern, which is the most cathodal (negative). By having the outer four electrodes to be less cathodal (not as negative), or even fully positive (anodal), the locus of cells that have suprathreshold activation can be shifted in two dimensions. With such constraining of the fields, the amplitude can be increased, driving the locus of activation deeper into the tissue, thereby creating a third dimensional effect.

In yet another aspect of the invention, the two-dimensional array of cathodes may be surrounded by an outer ring of anodes to keep the locus of activation contained and to shield outside tissue from activation.

In still another aspect of the invention, a combination of simultaneous and delayed cathodal pulses are applied on some electrodes in an array. Each pulse creates an area of subthreshold excitation, and the combination provides a controlled locus to the threshold for the production of action potentials.

These and other features and advantages of the present invention will be better understood by considering the following detailed description of the invention which is presented with the attached drawings.

BRIEF DESCRIPTION OF THE DRAWINGS

These and other advantages and features of the invention will become apparent upon reading the following detailed description and referring to the accompanying drawings in which like numbers refer to like parts throughout and in which:

FIGS. 16-25 depict various arrays of electrodes that may be used in accordance with the present invention.

DESCRIPTION OF THE PREFERRED EMBODIMENTS

Figure 8:
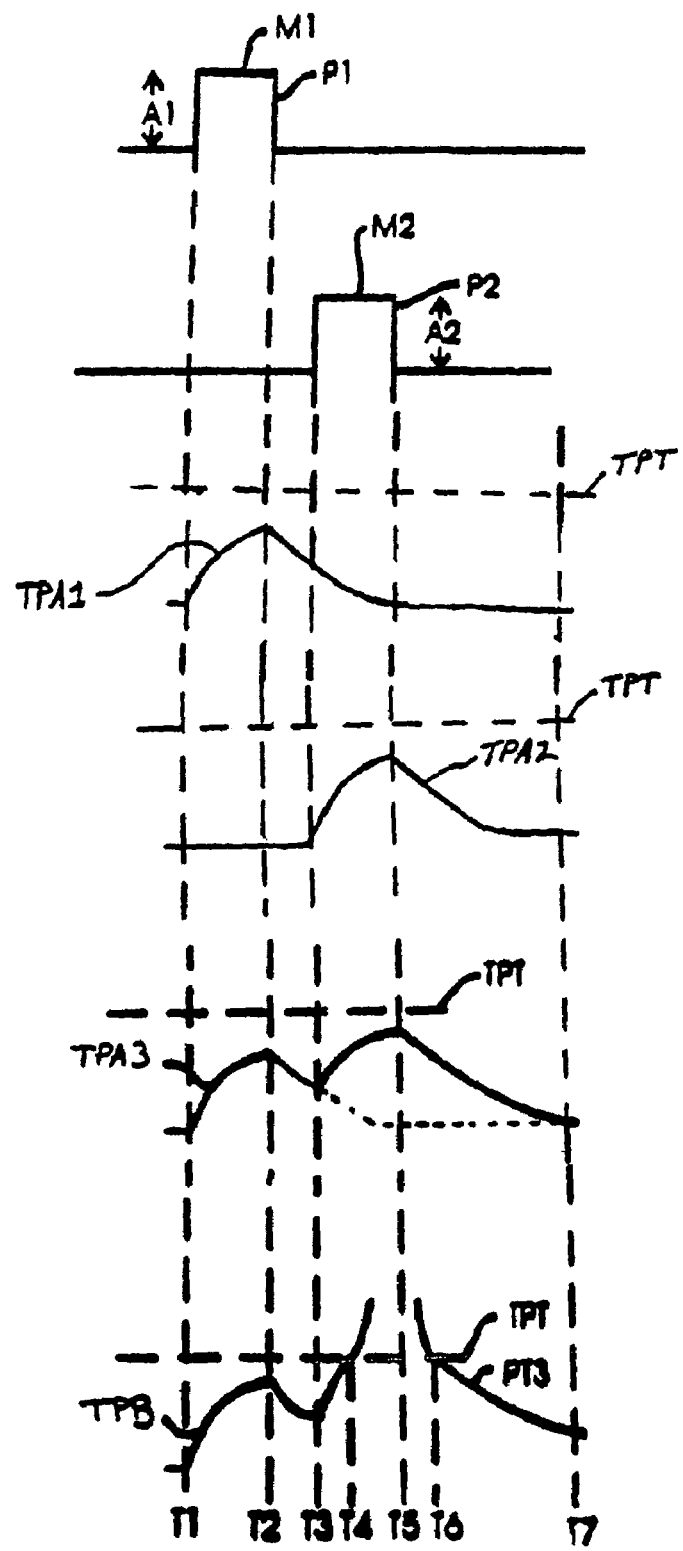
FIG. 8 is a timing diagram showing pulses applied to the first and second electrodes illustrated in FIG. 2 in relationship to the potential changes induced in tissue adjacent the electrodes.

Referring to FIG. 8, a single electrical pulse P1 can cause depolarization near a cathode in electrically excitable tissue which includes neural tissue or muscle tissue. Neural tissue includes peripheral nerves, ganglia, the spinal cord surface, deep spinal cord tissue, deep brain tissue, and brain surface tissue. Muscle tissue includes skeletal (red) muscle, smooth (white) muscle, and cardiac muscle. A locus includes a set of points in three-dimensional space and refers to a volume of cells or parts of cells. Due to the electrical characteristics of both the three-dimensional volume conductor and the membrane properties, the potentials outside and inside a neuron respond to the depolarization, usually with inverse exponential-type increases during the pulse and then attenuation over time after the pulse. The time constant for an isolated neuron membrane typically is 5-15 milliseconds (*Nerve, Muscle and Synapse* by Bernard Katz, circa 1972). For myelinated axons or muscle cells, it may be considerably shorter.

A living cell at any time has a transmembrane potential across its membrane. This transmembrane potential is typically defined as the potential in the inside of the cell with respect to the outside of the cell. At rest, a living cell has a constant transmembrane potential called a resting potential of approximately −60 mV to −90 mV, with the inside of the cell being more negative than outside of the cell. A variety of changes to the environment of the living cell can result in a corresponding change in the transmembrane potential.

A change in the environment that causes the inside of the cell to become less negative is referred to as a "depolarization" of the cell, and depolarization is then a positive change in the transmembrane potential. Similarly, a change in the environment that causes the inside of the cell to become more negative is referred to as a "hyperpolarization" of the cell, and hyperpolarization is a negative change in the transmembrane potential. An example of change in the environment of a living cell is when a voltage pulse is applied near the cell. Depending on the direction of the electric current caused by this stimulation pulse, the pulse can be either depolarizing or hyperpolarizing.

FIG. 8 shows an example pulse P1 that can cause time varying depolarization in a cell, and this depolarization from application of pulse P1 adjacent the cell can result in changes in a transmembrane potential TPA1. A further application of another pulse P2 adjacent the cell results in a portion of the curve TPA2. TPA3 is a superposition of the depolarizations caused by both pulses P1 and P2. The remaining depolarization from the prior application of pulse P1 between times T3 and T7 is shown by the dashed line curve in TPA3.

The transmembrane potential TPA1 is comprised of two components. The first component is the resting potential of the cell. This component is a constant gradient that exists across the membrane of the cell due to steady state ionic concentrations. Added to that first component is the depolarization that results from the application of pulse P1. Thus, transmembrane potential TPA1 is the sum total of the resting potential with the depolarization effects from application of pulse P1.

The sum total transmembrane potential TPA1 or TPA2 at any time must reach a certain transmembrane potential threshold TPT in order for the electrically excitable cell to get an action potential induced therein. The peak of potential TPA1 or TPA2 is below the transmembrane potential threshold TPT, and thus potential TPA1 or TPA2 can be characterized as a subthreshold potential. As a result, the potential changes from pulses P1 or P2 alone fail to produce an action potential in that cell. Even when pulses P1 and P2 occur with a time delay (T3-T2), the transmembrane potential TPA3 may still not reach the transmembrane potential TPT.

Action potential is an all-or-none, nonlinear phenomenon, caused by opening of sodium gates, inrush of sodium ions, and a delayed opening of potassium gates and a restoration of the membrane potential. In general, a certain amount of charge must be passed at the electrodes (amplitude [Volts]/resistance [Ohms]×pulse width [time]) in order to cause enough depolarization for an action potential to begin. There is a reciprocal relationship between amplitude and pulse width: the product must reach a certain value before the transmembrane potential threshold is reached. This relationship does not reach the Volts=0 axis. There is a certain minimum voltage needed, called rheobase, before an action potential can happen.

Basic neurophysiological principles, called "electrotonus", show that in any volume of electrically excitable tissue, if two or more depolarizing pulses tending to induce action potentials, each of which alone is insufficient to bring the cells to threshold, arrive closely together in time, at least part of their effect is additive, i.e., the memory of the first pulse is still present when the second pulse arrives. If the sum of the potentials (distorted by resistive and capacitive properties of the surroundings and the cell membranes) can get some cells depolarized to threshold, then an action potential will start in those cells. A reference that explains these principles of "electrotonus" including the creation of subthreshold potentials is *Medical Physiology*, 13th Edition, Vol. 1, by Vernon B. Mountcastle, C. V. Mosby Co., 1974.

Still referring to FIG. 8, the inducement of an action potential in a cell is illustrated by a transmembrane potential TPB reaching the transmembrane potential threshold TPT at time T4. TPB can be characterized as a suprathreshold potential, and the nerve tissue has an action potential started when TPB reaches the transmembrane potential threshold (at time T4). The transmembrane potential TPB is comprised of the constant resting potential and a depolarization that is sufficient enough to push the total transmembrane potential TPB above the transmembrane potential threshold. TPB at time T4 has sufficient depolarization to go above the transmembrane potential threshold because the amplitude of pulse P2 may have either been larger than in the case of the subthreshold transmembrane potential TPA2 or have come soon enough before the memory of the effect of pulse P1 has subsided.

Figure 1:
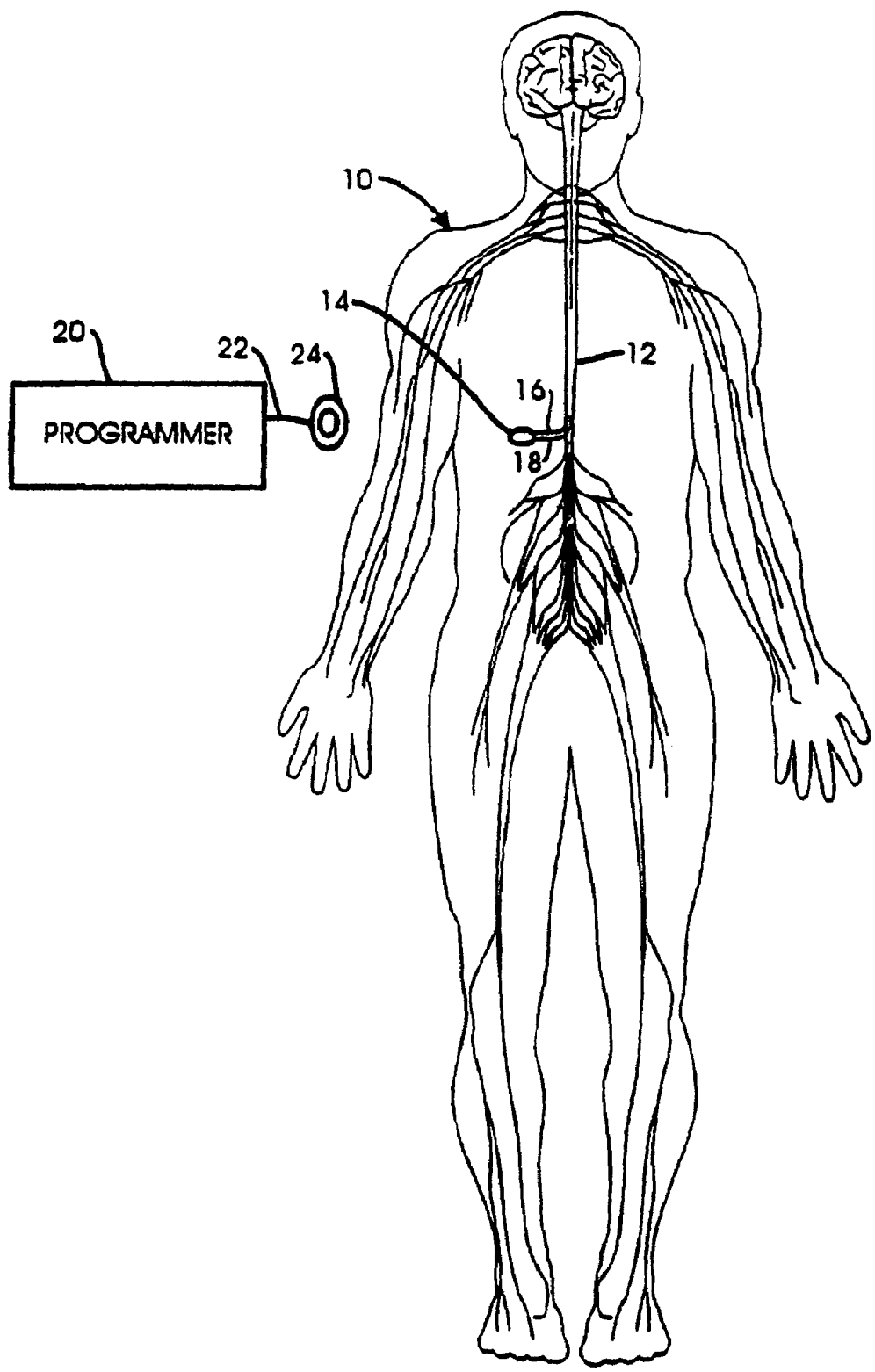
FIG. 1 is a diagrammatic view of a patient in which a preferred form of apparatus for SCS made in accordance with the invention has been implanted.
Figure 2:
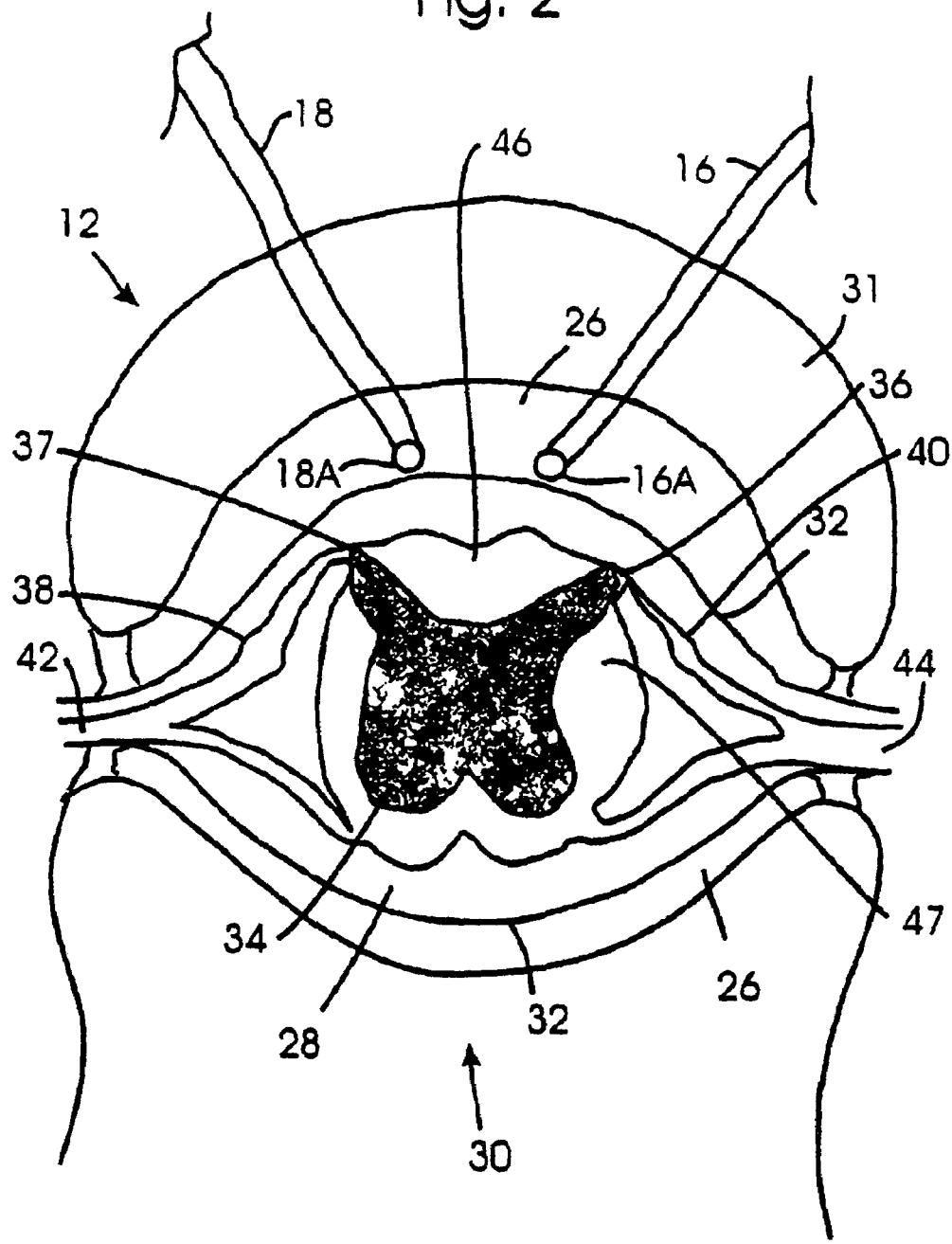
FIG. 2 is a cross-sectional view of an exemplary spinal column showing a typical position at which electrodes made in accordance with the preferred practice of the invention have been implanted in the epidural space.

FIG. 1 is a schematic view of a patient 10 having an implant of a neurological stimulation system employing a preferred form of the present invention to stimulate spinal cord 12 of the patient. The preferred system employs an implantable pulse generator 14 to produce a number of independent stimulation pulses which are sent to spinal cord 12 by insulated leads 16 and 18 coupled to the spinal cord by electrodes 16A and 18A (FIG. 2). Electrodes 16A and 18A also can be attached to separate conductors included within a single lead.

Implantable pulse generator 14 preferably is a modified ITREL II implantable pulse generator available from Medtronic, Inc. with provisions for multiple pulses occurring either simultaneously or with one pulse shifted in time with respect to the other, and having independently varying amplitudes and pulse widths. This preferred system employs a programmer 20 which is coupled via a conductor 22 to a radio frequency antenna 24. This system permits attending medical personnel to select the various pulse output options after implant using radio frequency communications. While the preferred system employs fully implanted elements, systems employing partially implanted generators and radio-frequency coupling may also be used in the practice of the present invention (e.g., similar to products sold by Medtronic, Inc. under the trademarks X-trel and Mattrix).

FIG. 2 is a cross-sectional view of spine 12 showing implantation of the distal end of insulated leads 16 and 18 which terminate in electrodes 16A and 18A within epidural space 26. The electrodes may be conventional percutaneous electrodes, such as PISCES® model 3487A sold by Medtronic, Inc. Also shown is the subdural space 28 filled with cerebrospinal fluid (cfs), bony vertebral body 30, vertebral arch 31, and dura mater 32. The spine also includes gray matter 34 and dorsal horns 36 and 37 and white matter, for example, dorsal columns 46 and dorsal lateral columns 47.

Stimulation pulses are applied to electrodes 16A and 18A (which typically are cathodes) with respect to a return electrode (which typically is an anode) to induce a desired area of excitation in the spine 12 having nerve tissue capable of producing action potentials. (A cathode has a more negative potential with respect to an anode, and the electrical current caused by the cathode tends to induce an action potential whereas the electrical current caused by the anode tends to inhibit an action potential.) The return electrode, for example a ground or other reference electrode, is also present but is not shown in the cross sectional view of spine 12 because the return electrode is located typically at a different plane from the shown cross section of FIG. 2. For example, the return electrode may be located near a point up or down the line along the spinal column 12 or at a more remote part of the body 10 carrying the spine, such as at the metallic case of the pulse generator 14. Alternatively, more than one return electrode may be present in the body. There can be a respective return electrode for each cathode such that a distinct cathode/anode pair is formed for each cathode.

Referring to FIG. 8, pulse P1 is applied to electrode 18A (FIG. 2) and pulse P2 is applied to electrode 16A (FIG. 2). Pulses P1 and P2 have a timing relationship. For optimal operation of the present invention with the application of the principle of "electrotonus", pulses P1 and P2 should not overlap in time. For example, the end of pulse P1 at time T2 and the start of pulse P2 at time T3 in FIG. 8 are displaced by a predetermined time period less than 500-2000 microseconds, and preferably less than 50-500 microseconds. Amplitude A1 of P1 is adjustable independently from amplitude A2 of pulse P2. The pulse widths of pulses P1 and P2 also are independently adjustable. Widening the pulse widths of each pulse (i.e., P1 and P2) can also expand the loci of depolarizations, just like increasing amplitude, either voltage or current amplitude.

Figure 9:
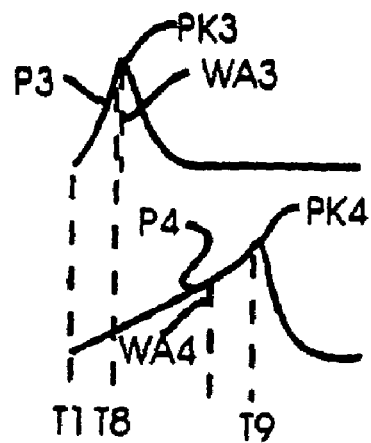
FIGS. 9 and 10 are timing diagrams illustrating alternative forms of pulses applied to the electrodes illustrated in FIG. 2.
Figure 10:
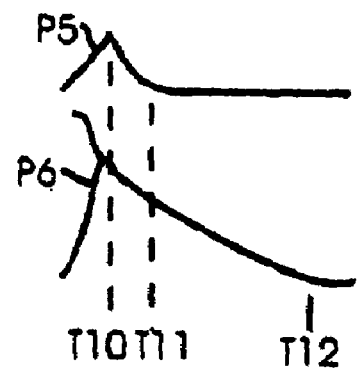

The pulses P1 and P2 also could have other time delay relationships in order to accomplish the goals of the present invention. Referring to FIG. 9, pulses P3 and P4, having different rise times, could be used. P3 has a rise time from T1 to T8 and P4 has a rise time from T1 to T9. Referring to FIG. 10, pulses P5 and P6, having different fall times, could be used. P5 has a fall time from T10 to T11, and P6 has a fall time from T10 to T12. The weighted average time WA3 of pulse P3 (FIG. 9) is displaced from the weighted average time WA4 of pulse P4 by a predetermined time period of less than 500-2000 microseconds and preferably less than 50-500 microseconds. A weighted average time is the integral of a pulse over the pulse interval divided by the pulse amplitude of the pulse interval. The rise time and fall time of a pulse can affect the weighted average time of the pulse.

Similarly, the peak PK3 of pulse P3 is displaced from the peak PK4 of pulse P4 by a predetermined time period of less than 500-2000 microseconds and preferably less than 50-500 microseconds. The rise time of a pulse can affect the peak time of the pulse. Objectives of the invention also can be achieved using combinations of the foregoing timing relationships. For example, the time delay between the first pulse and the second pulse can be the time difference between a first weighted average time of the first pulse and a second weighted average time of the second pulse. Alternatively, the time delay can be the time difference between a first peak time of the first pulse and a second peak time of the second pulse.

Figure 3:
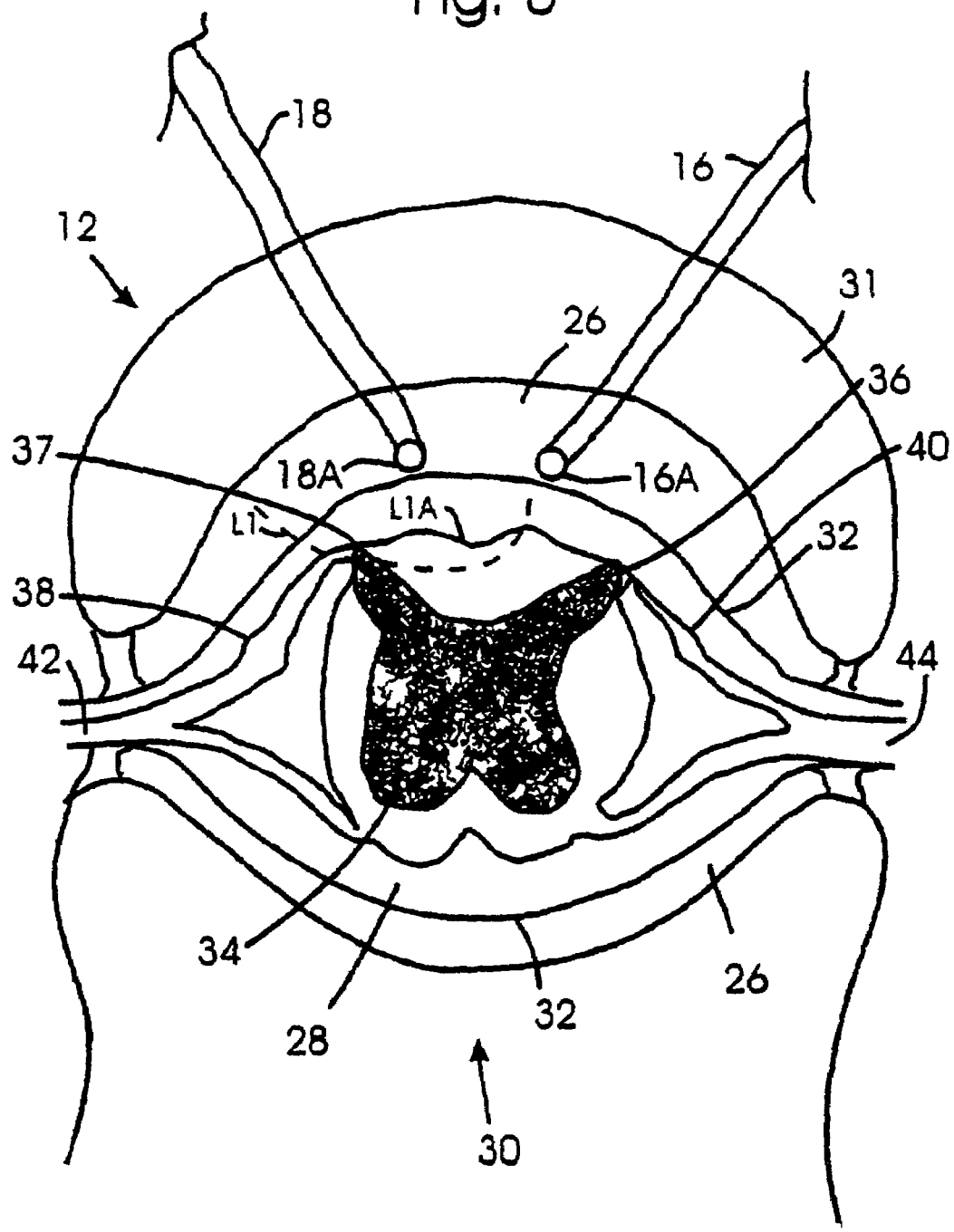
FIG. 3 is a cross-sectional view like FIG. 2 showing locus of potential changes induced in cells of the spinal cord from a pulse applied to a first one of two electrodes.

Referring to FIGS. 3 and 8, line L1 represents the edge of a three-dimensional locus L1A of cells in excitable tissue in which pulse P1 applied to electrode 18A results in a transmembrane potential which can be represented by curve TPA1 of FIG. 8. That transmembrane potential is less than the transmembrane potential threshold TPT for cells of interest in that locus. That transmembrane potential is comprised of a constant resting potential and a depolarization caused by application of pulse P1 to electrode 18A. Thus, locus L1A, which results from pulse P1 being applied to electrode 18A without a recent pulse being applied to electrode 16A is an area having subthreshold potential since TPA1 is less than the transmembrane potential threshold TPT.

Figure 4:
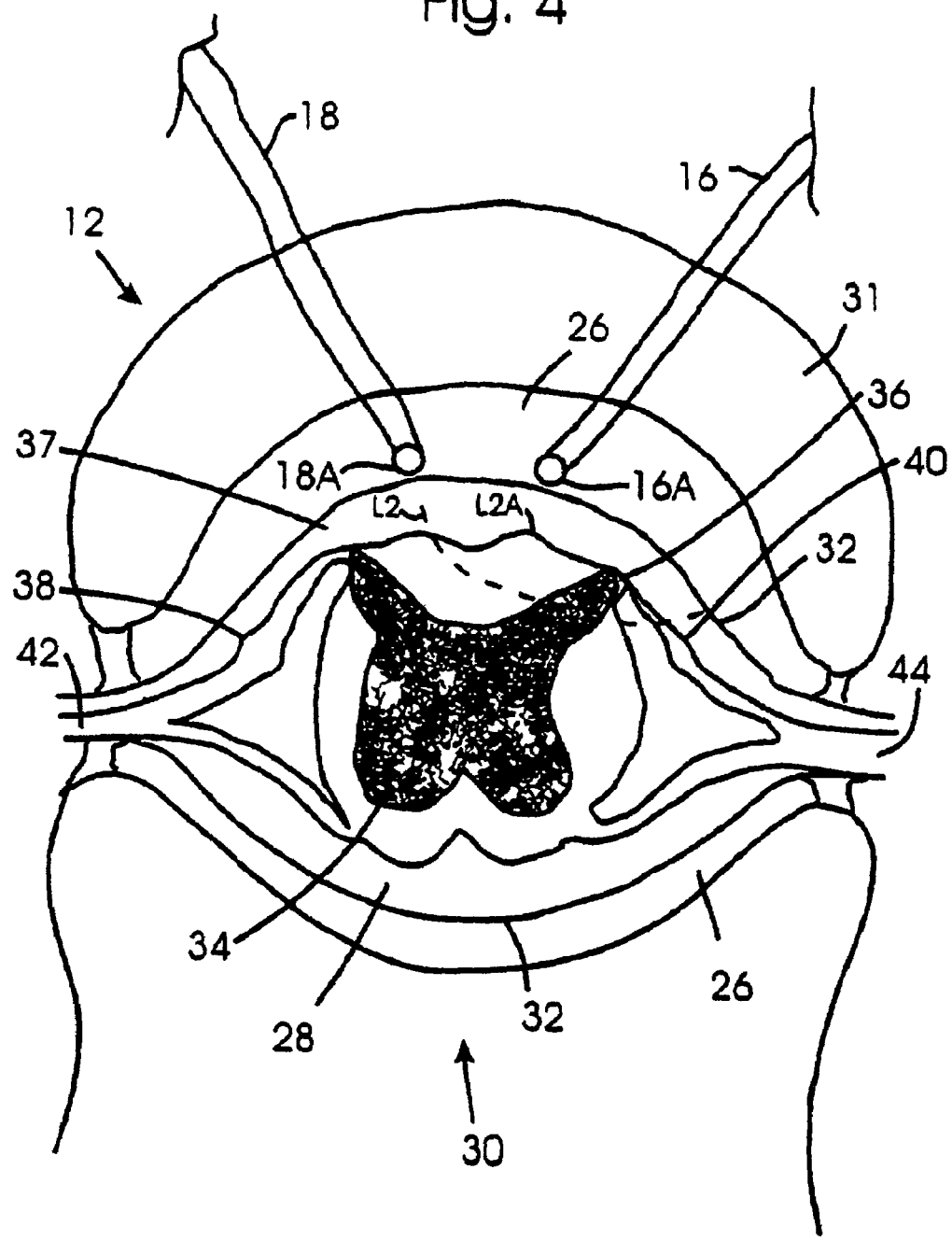
FIG. 4 is a view like FIG. 3 showing the locus of potential changes induced in cells of the spinal cord from the application of a pulse to the second of the electrodes.

Similarly, referring to FIGS. 4 and 8, line L2 represents the edge of another three-dimensional locus L2A in which the application of pulse P2 to electrode 16A results in a transmembrane potential which also can be represented by the transmembrane potential curve TPA2 of FIG. 8. That transmembrane potential is less than the transmembrane potential threshold TPT for cells of interest in that locus. That transmembrane potential is the sum of a constant resting potential and a depolarization potential caused by application of pulse P2 to electrode 16A. Thus, locus L2A, which results from pulse P2 being applied to electrode 16A without a recent pulse being applied to electrode 18A is also an area of subthreshold potential since TPA2 is less than the transmembrane potential threshold TPT.

Figure 5:
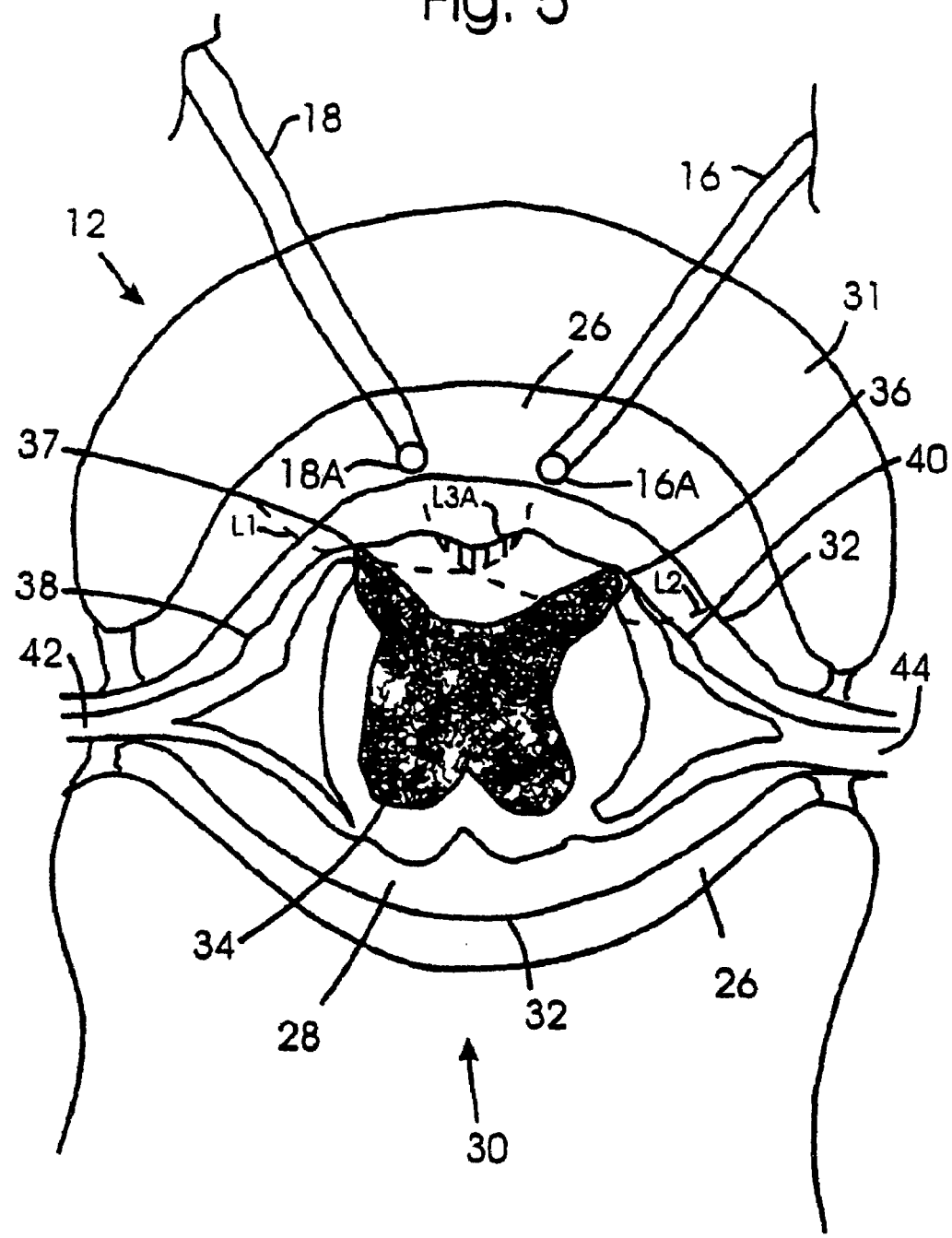
FIG. 5 is a view like FIG. 4 showing the combined loci in the spinal cord at which potential changes are induced from pulses applied to the first and second electrodes.

FIG. 5 illustrates a locus L3A representing the intersection of loci L1A and L2A in which the combined potentials induced in locus L3A from pulses P1 and P2 create an action potential in cells of interest in locus L3A as illustrated by the transmembrane potential TPB in FIG. 8. The total potential in cells in locus L1A outside locus L3A is illustrated by the transmembrane potential TPA1 in FIG. 8. Since TPA1 is lower than the transmembrane potential threshold TPT, the total potential is a subthreshold potential, and there is no action potential created in cells in locus L1A outside L3A. The total potential created in cells in locus in L2A outside L3A is illustrated by transmembrane potential TPA2 in FIG. 8. Again, the total potential is a subthreshold potential, and there is no action potential created in cells in locus L2A outside L3A.

The suprathreshold potential induced in cells in locus L3A results from a superposition of the subthreshold potentials TPA1 and TPA2 created in that area by excitation from a pulse applied to electrode 16A and from another pulse applied to electrode 18A. Locus L3A has nerve cells that get action potentials resulting from this suprathreshold potential induced in that locus. The total potential in cells in locus L3A is illustrated by the transmembrane potential TPB of FIG. 8. That transmembrane potential is comprised of the constant resting potential and the superposition of depolarizations from application of pulse P1 to electrode 18A and pulse P2 to electrode 16A.

Figure 6:
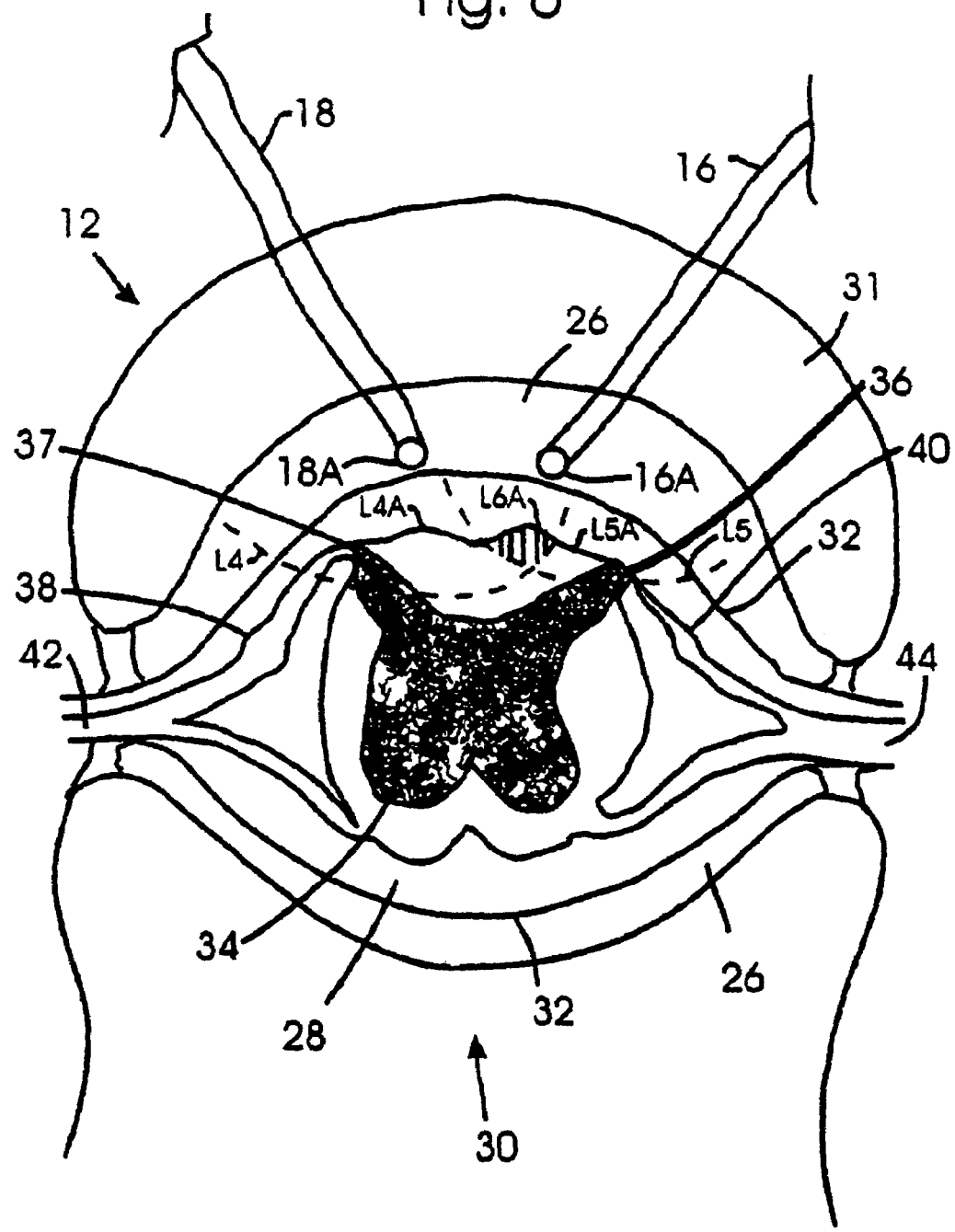
FIG. 6 is a view like FIG. 5 showing the alteration of the loci due to increase in the amplitude of the pulse applied to the first electrode and a decrease in amplitude of the pulse applied to the second electrode.

Referring to FIGS. 6 and 8, line L4 represents the edge of another three-dimensional locus L4A having subthreshold potential resulting from the application of a pulse P1 to electrode 18A having an amplitude greater than amplitude A1. Line L5 represents the edge of another three-dimensional locus L5A having subthreshold potential resulting from the application of a pulse P2 to electrode 16A having an amplitude less than amplitude A2. The intersection of loci L4A and L5A creates a locus L6A in which a suprathreshold action potential results from a superposition of subthreshold potentials created by application of pulses P1 and P2. Locus L6A is moved mostly to the right relative to locus L3A shown in FIG. 5. Action potentials are not induced outside locus L6A since the area outside that locus has subthreshold potentials.

Figure 7:
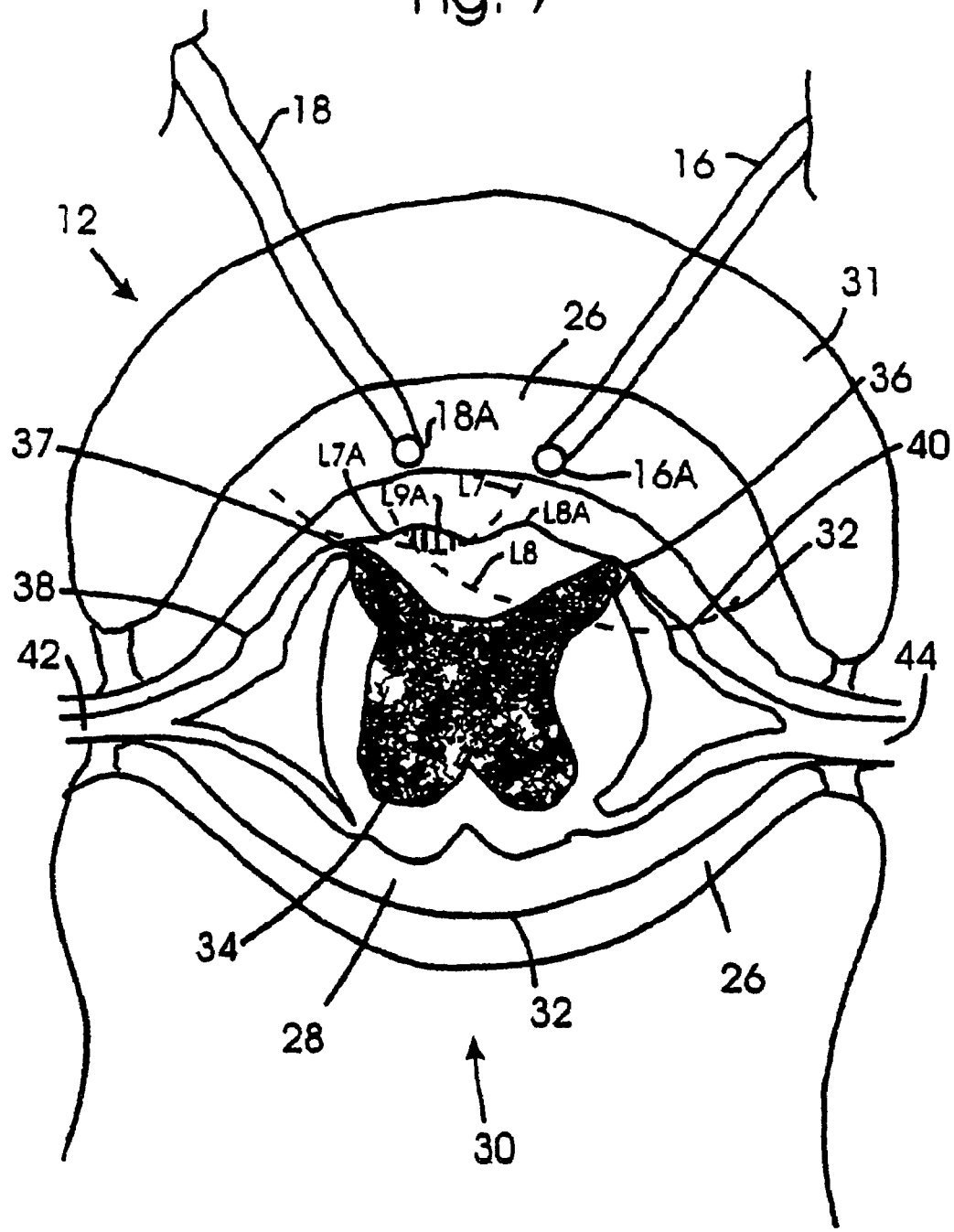
FIG. 7 is a view like FIG. 6 showing the alteration of the loci due to an increase in amplitude of the pulse applied to the second electrode and a decrease in amplitude of the pulse applied to the first electrode.

Referring to FIGS. 7 and 8, line L8 represents the edge of another three-dimensional locus L8A having subthreshold potential resulting from the application of a pulse P2 to electrode 16A having an amplitude greater than amplitude A2. Line L7 represents the edge of another three-dimensional locus L7A having subthreshold potential resulting from the application of a pulse P1 to electrode 18A having an amplitude less than amplitude A1. The intersection of loci L7A and L8A creates a locus L9A in which a suprathreshold action potential is induced from a superposition of subthreshold potentials created by application of both pulses P1 and P2. It will be noted that the locus L9A is moved to the left compared with locus L3A shown in FIG. 5. Action potentials are not induced outside locus L9A since the area outside that locus has subthreshold potentials.

A benefit of utilizing the neurophysiological principle of "electrotonus" is that the area of suprathreshold potential can be controlled by varying the time delay between application of the two pulses to each respective driven electrode for creating the areas of subthreshold potential. Referring to FIG. 8, this time delay can be the time period between the end of pulse P1 at time T2 and the start of pulse P2 at time T3.

Principles of "electrotonus" indicate that a potential for any nerve cell decays with a RC time constant after a stimulation pulse has been applied to that nerve cell. R is a resistive value determined by the resistive characteristic for that nerve cell, and C is a capacitive value determined by the capacitive characteristic for that nerve cell.

Because of this memory effect of electrotonus, the transmembrane potential created within a nerve cell by a pulse starts to decay at the end of the excitation pulse, and this transmembrane potential is a function of time. By taking advantage of this time variation of the transmembrane potential, the area of suprathreshold potential can be adjusted by correspondingly varying the time delay between the pulses that are applied to two electrodes that each produce a subthreshold area.

Figure 12:
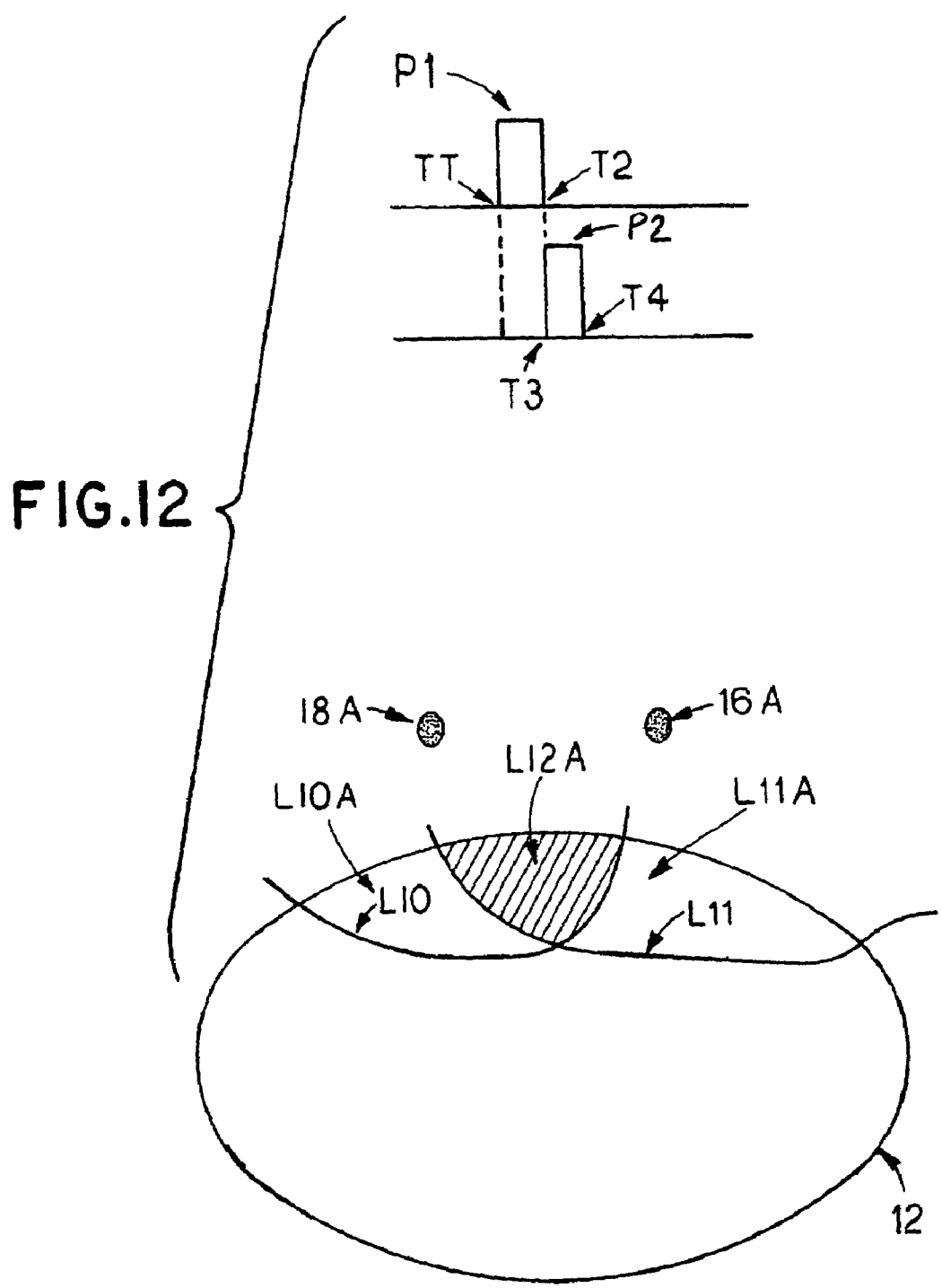
FIG. 12 shows the suprathreshold potential area generated from application of two pulses to two electrodes where the two pulses having a first time delay between the end of the first pulse and the start of the second pulse.

This benefit is further illustrated in FIGS. 12-15 where elements similar to elements in the prior figures are labeled with the same numeric label. FIG. 12 illustrates the case where the pulses applied to the two cathodes follow closely in time. Element 12 is a simplified illustration of electrically excitable tissue such as spinal cord tissue. Pulse P2 immediately follows after the end of pulse P1, and the time delay between the end of pulse P1 at T2 and the start of pulse P2 at T3 is small in this case.

Line L10 represents the isopotential line defining a subthreshold area L10A created by application of pulse P1 at electrode 18A. Line L11 represents the isopotential line defining another subthreshold area L11A created by application of pulse P2 at electrode 16A. (A return electrode is not shown in FIGS. 12-15 since that electrode is typically located on a different plane from the shown tissue plane 12 or on a more remote location on the body carrying the tissue 12 such as at the metallic case of the pulse generator 14 of FIG. 1.) Each isopotential line varies with time and progresses away from the electrode producing that isopotential line during the application of a pulse to that electrode and recedes back toward that electrode after the completion of the pulse by the principle of "electrotonus". In FIG. 12, the isopotential lines L10 and L11 are what result at the end of pulse P2 at time T4. These individual subthreshold areas by themselves do not have sufficient potential changes to induce an action potential within tissue 12. However, a superposition of the subthreshold potential areas at time T4 creates an area L12A of suprathreshold potential that is greater than the transmembrane potential threshold such that nerve cells within that area have an action potential induced therein.

Figure 13:
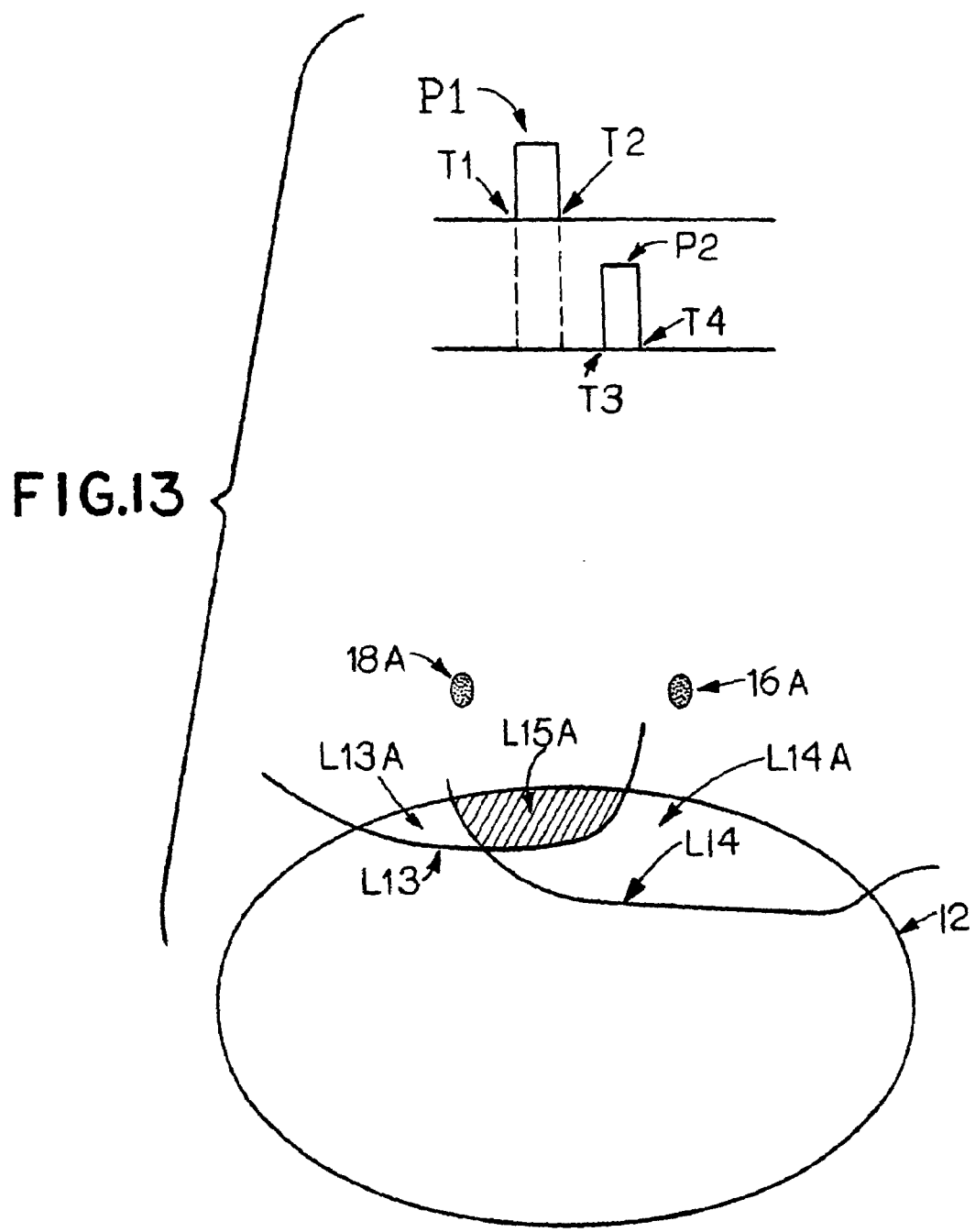
FIG. 13 shows the suprathreshold potential area generated from application of two pulses to two electrodes where the two pulses have a second time delay between the end of the first pulse and the start of the second pulse, with the second time delay being greater than the first time delay of FIG. 12.

FIG. 13 shows a case where the two pulses P1 and P2 are more separated in time than the case illustrated in FIG. 12. The transmembrane potentials in FIG. 13 that are created in electrically excitable tissue 12 are those that remain at the end of pulse P2 at time T4. By that time, the application of pulse P1 was already completed at time T2. Isopotential line L13 defines the subthreshold area L13A that remains from the application of pulse P1 to electrode 18A by time T4. Isopotential line L14 defines the subthreshold area L14A that is created by application of pulse P2 to electrode 16A by time T4.

These individual subthreshold areas by themselves do not have sufficient potential changes to induce an action potential. However, a superposition of the subthreshold potential areas creates an area L15A of suprathreshold potential that is greater than the transmembrane potential threshold such that nerve cells within that area have an action potential induced therein. Note that the area of suprathreshold potential L15A of FIG. 13 differs from the area of suprathreshold potential L12A of FIG. 12 because of the larger time delay between the end of pulse P1 at T2 and the start of pulse P2 at T3 in FIG. 13 than in FIG. 12.

Figure 14:
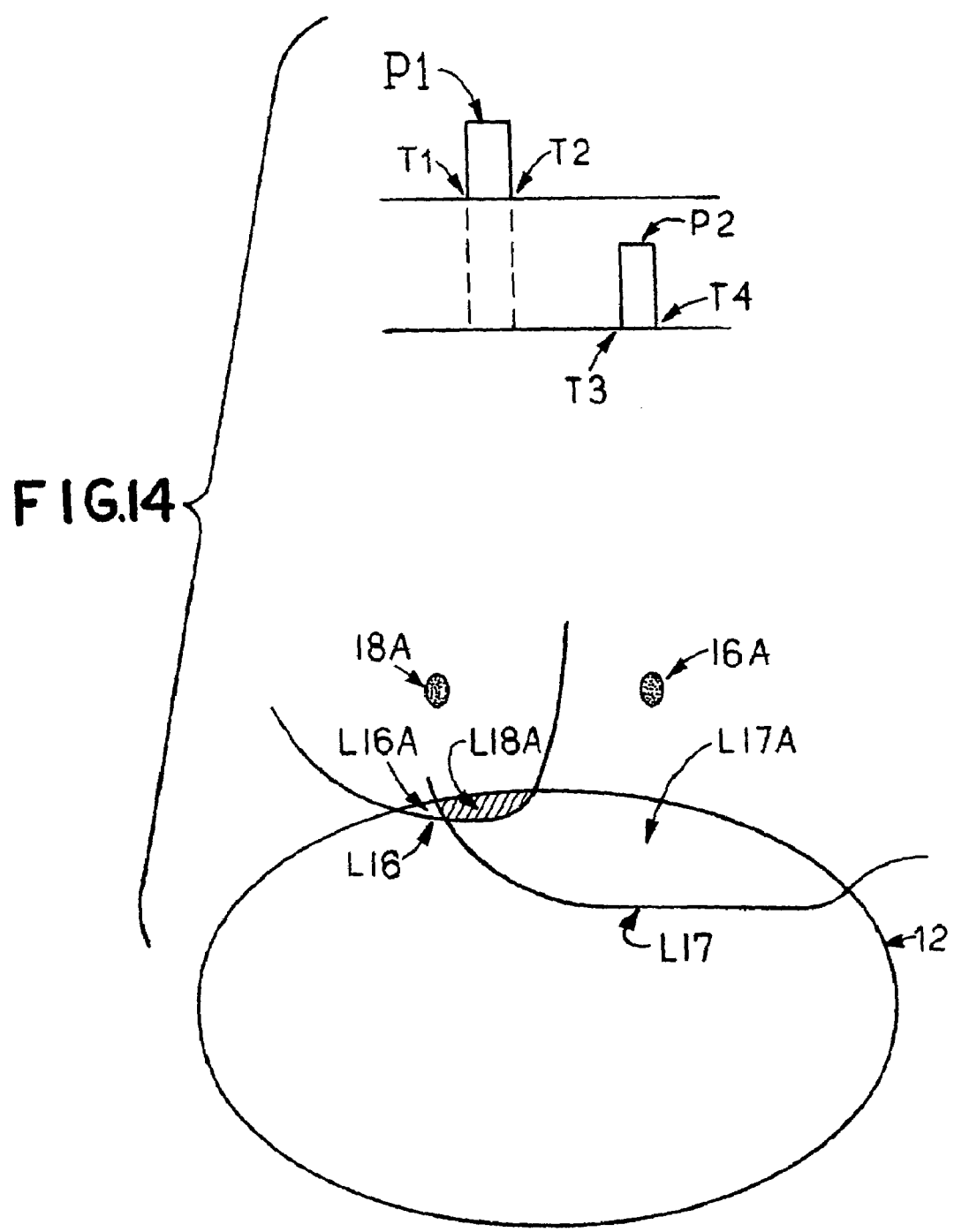
FIG. 14 shows the suprathreshold potential area generated from application of two pulses to two electrodes where the two pulses have a third time delay between the end of the first pulse and the start of the second pulse, with the third time delay being greater than the second time delay of FIG. 13.

Similarly, FIG. 14 shows a case where the two pulses P1 and P2 are still even more separated in time than those of FIG. 13. FIG. 14 shows the isopotential lines that are created by pulses P1 and P2 at the end of pulse P2 at time T4. The isopotential line L16 defines the subthreshold area L16A created by the application of pulse P1 at electrode 18A by time T4, and the isopotential line L17 defines the subthreshold area L17A created by the application of pulse P2 at electrode 16A by time T4.

The individual subthreshold areas within isopotential lines L16 and L17 by themselves do not have sufficient potential changes to induce an action potential. However, a superposition of subthreshold potential areas creates an area L18A of suprathreshold potential that is greater than the transmembrane potential threshold such that nerve cells within that area have an action potential induced therein. Note that because of the larger delay between pulses P1 and P2, isopotential line L16 has receded further toward electrode 18A by the end of pulse P2 at time T4, and the area L18A of suprathreshold potential has decreased and has shifted more toward electrode 18A.

Figure 15:
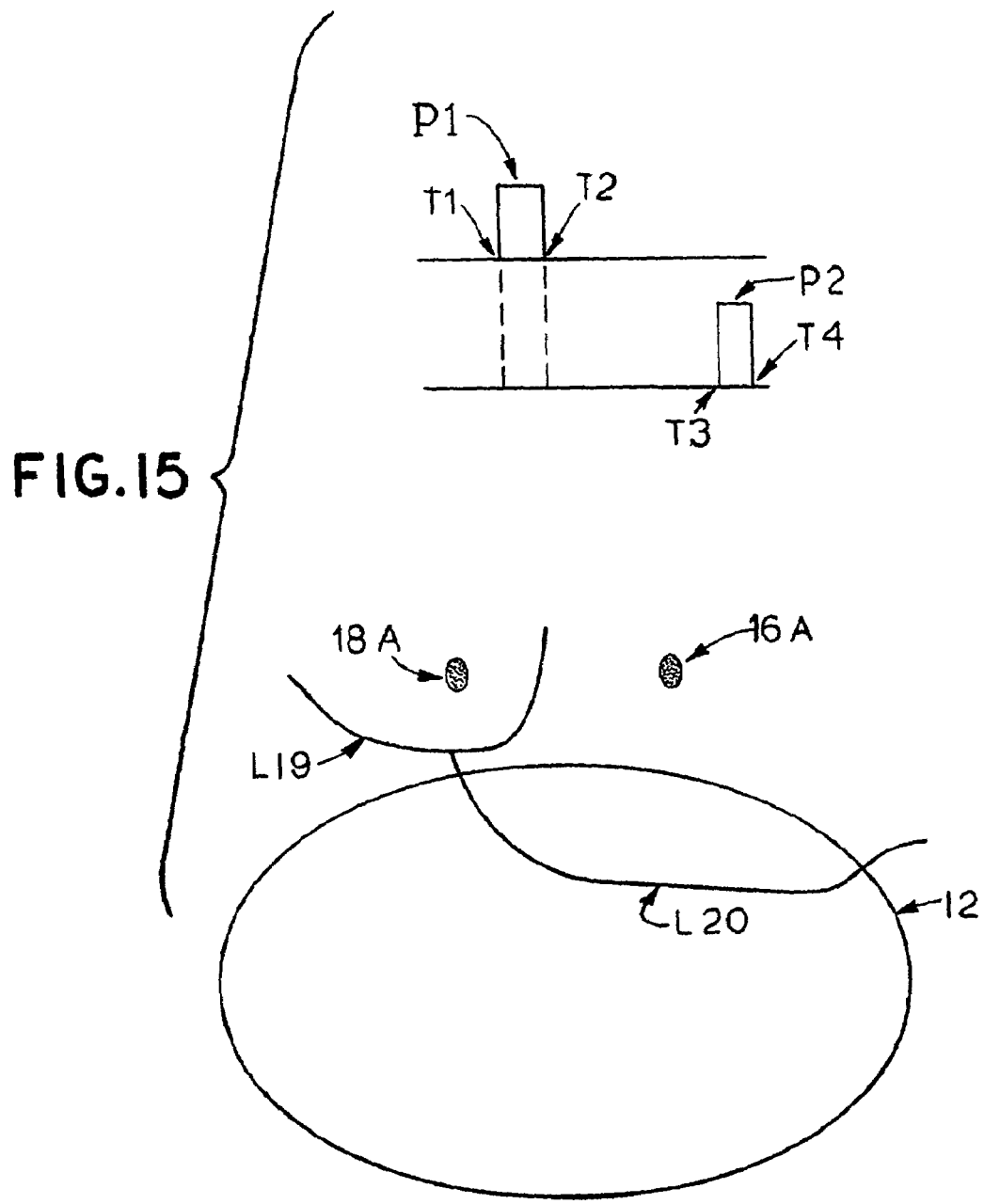
FIG. 15 shows the suprathreshold potential area generated from application of two pulses to two electrodes where the two pulses have a fourth time delay between the end of the first pulse and the start of the second pulse, with the fourth time delay being greater than the third time delay of FIG. 14.

Finally, FIG. 15 shows a case where pulse P1 and P2 have a time delay sufficiently far enough such that no area of suprathreshold potential is created within the electrically excitable tissue 12. Isopotential line L19 is the result of application of pulse P1 at electrode 18A by the end of pulse P2 at time T4, and isopotential line L20 is the result of application of pulse P2 at electrode 16A by time T4. Because of the large delay between pulses P1 and P2, isopotential line L19 has receded so far back toward electrode 18A that there is no area of superposition of the two subthreshold areas created by isopotential lines L19 and L20 within tissue 12.

The ability to move the locus in which action potentials are induced by controlling the area of superposition of subthreshold potential areas is an important feature. In many therapies, it is important to prevent action potentials being induced in gray matter 34 or dorsal horns 36 and 37, dorsal roots 38 and 40, dorsal lateral columns 47 or peripheral nerves 42 and 44 in order to minimize the possibility of causing pain, motor effects, or uncomfortable paresthesia. With the described techniques, the locus in which action potentials are induced (e.g., L3A, L6A, L9A, L12A, L15A, or L18A) can be manipulated to a desired area of the dorsal columns 46 without inducing action potentials in dorsal horns 36 and 37, gray matter 34 or dorsal lateral columns 47 or dorsal root ganglia 38 and 40. Moreover, the ability to move the locus in which action potentials are induced drastically reduces the accuracy necessary for surgically implanting electrodes 16A and 18A, and may eliminate the need for surgical lead revisions.

Another advantageous result from being able to determine the locus of excitation by controlling the area of suprathreshold potential from superposition of subthreshold potential areas is that the location of the two driven electrodes 16A and 18A and the return electrode with respect to each other is not critical to the practice of this invention. In contrast to the invention disclosed by Holsheimer et al. in U.S. Pat. No.

5,501,703, the two driven electrodes and the return electrode in the present invention are not optimally spaced in line with respect to each other. In fact, the return electrode of the present invention can be located remotely from the driven electrodes 16A and 18A near a point up or down the spinal column or another part of the body carrying the spine being excited. Alternatively, there may be more than one return electrode within the body.

Figure 11:
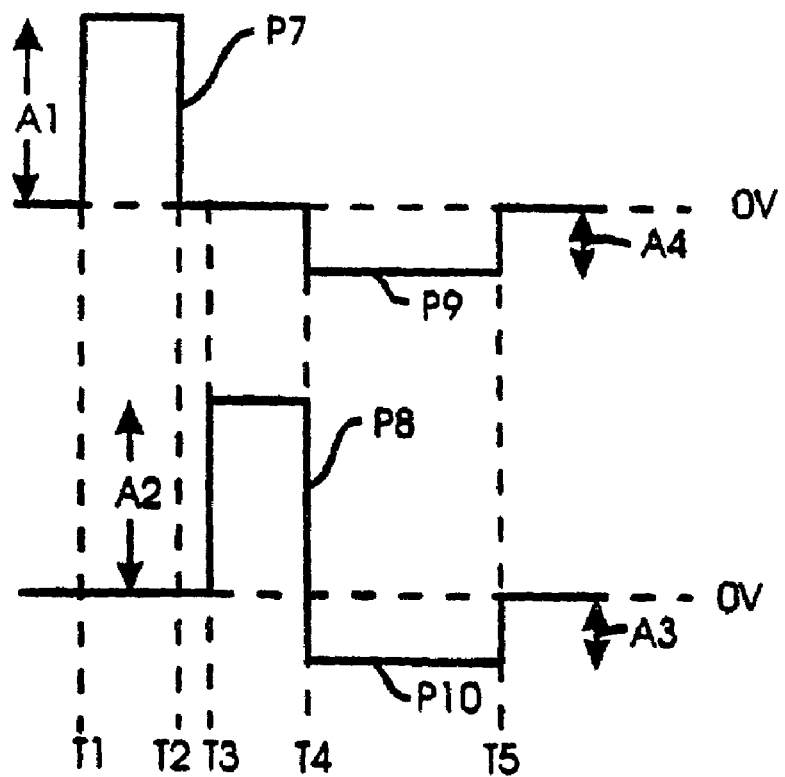
FIG. 11 is a timing diagram illustrating a preferred form of pulses applied to the electrodes shown in FIG. 2.

FIG. 11 illustrates a preferred timing relationship between pulse P7 applied to electrode 18A and pulse P8 applied to electrode 16A. Currently available pulse generators use a biphasic pulse to insure no net direct current flows into the tissue. This is known as charge-balanced pulsing, and is accomplished by driving the pulse negative for a duration of time. For example, in FIG. 11, pulse P8 has a net charge delivered proportional to A2*(T4−T3). This injected charge is balanced by the negative pulse P10, whose charge is proportional to A3*(T5−T4), where A3<<A2 and (T5−T4)>> (T4−T3). Similar principles apply even if the first and second pulses are not of constant amplitude.

In a preferred embodiment, pulse P7 may be generated with a trailing negative pulse P9 from time T4 to time T5, so that the output on electrode 18A is substantially at neutral or 0 potential until the termination of pulse P8 at time T4. Having this delay in charge balancing prevents the loss of potential in adjacent tissue that otherwise would occur if pulse P9 immediately followed pulse P7 and overlapped with pulse P8, thus offsetting the benefit of pulse P8. At time T4 both negative pulses P9 and P10 begin in order to maintain the charge balance in tissue adjacent to the respective electrodes 18A and 16A.

In another embodiment of the present invention, the present invention utilizes an array of electrodes to more finely control the shape of the field of excitation. These electrodes provide multi-channel stimulation of the desired treatment area. Multi-channel stimulation generally refers to the stimulation of several sites at differing pulse parameters including, for example and without limitation, pulse amplitude, pulse width, pulse frequency, pulse shape, pulse rise, pulse fall, pulse peak, and pulse polarity. These pulses may be either voltage or current pulses. For example, if one site receives a voltage or current pulse, and then another site gets a pulse at the same time, an overlapping time, or a separate time. The stimulation and steering techniques discussed above may be used to achieve suprathreshold potentials within the desired treatment areas. The field of excitation may be created and controlled using any number of techniques, including but not limited to, simultaneous pulses of two cathodal amplitudes and one anode, paired (delayed) pulses using two or more electrodes, a combination of simultaneous and paired (delayed) pulses among various electrodes, and conventional full polarity pulses of anodes and cathodes. Each of these techniques are discussed herein in further detail.

Figure 16:
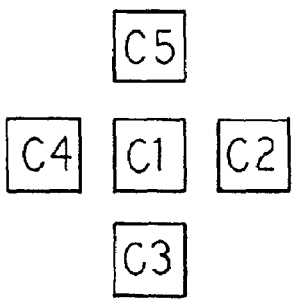
Figure 18:
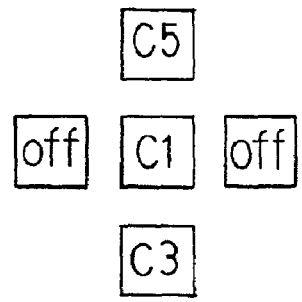
Figure 17:
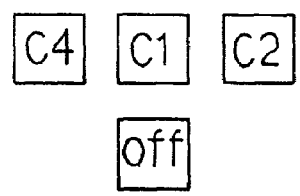
Figure 19:
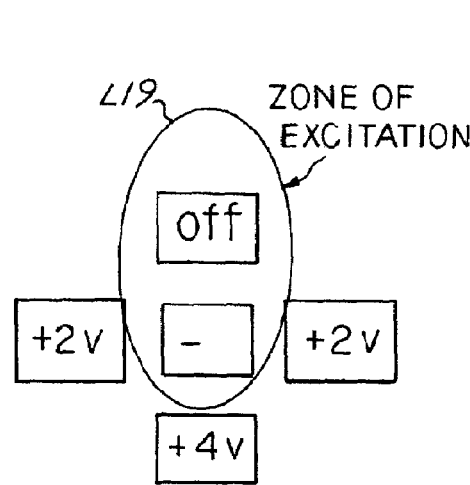
Figure 20:
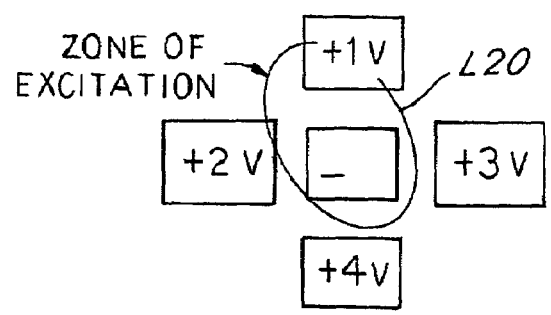

FIG. 16 shows a way to perform two-dimensional steering using an array 1600 of electrodes. These electrodes may be placed on a paddle lead or may be positioned across three adjacent percutaneous leads. Array 1600 may include a central cathode C1 and up to four surrounding anodes C2-C5. Simultaneous anodal pulses can then be delivered, each with their own potential, to the surrounding electrodes C2-C5. Advantageously, the electric field may be steered in any number of directions over a 2-dimensional space. As exemplified in FIG. 17, the effect may be steered from left to right by using electrodes C1, C2 and C4 and turning off electrodes C3 and C5. Further, as exemplified in FIG. 18, the effect may be steered from top to bottom by using electrodes C1, C3 and C5. FIG. 19 illustrates a method to shield activation of cells in a lower direction and to maintain the field of excitation in the middle and slightly upward. The field of excitation L19 is skewed by using only anodal electrodes C2-C4, where electrode C3 is stronger in voltage than electrodes C2 and C4. FIG. 20 illustrates steering of field L20 along a diagonal by using surrounding electrodes C2-C5 but with varying voltages.

Figure 21:
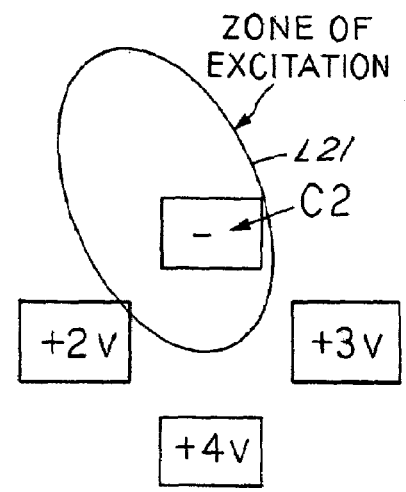

As shown in FIG. 21, central electrode C1 may also be eliminated altogether. In this case, one of the remaining electrodes, say C2 is the most cathodal (−), and the remaining three electrodes C2-C4 can be programmed to have three equal or different anodal voltages to provide the necessary steering of the field L21. Although the currents from electrode C2 move off in the other direction in a less controlled manner, this embodiment advantageously avoids current waste that would be present with a nearby central cathode C1.

Figure 22:
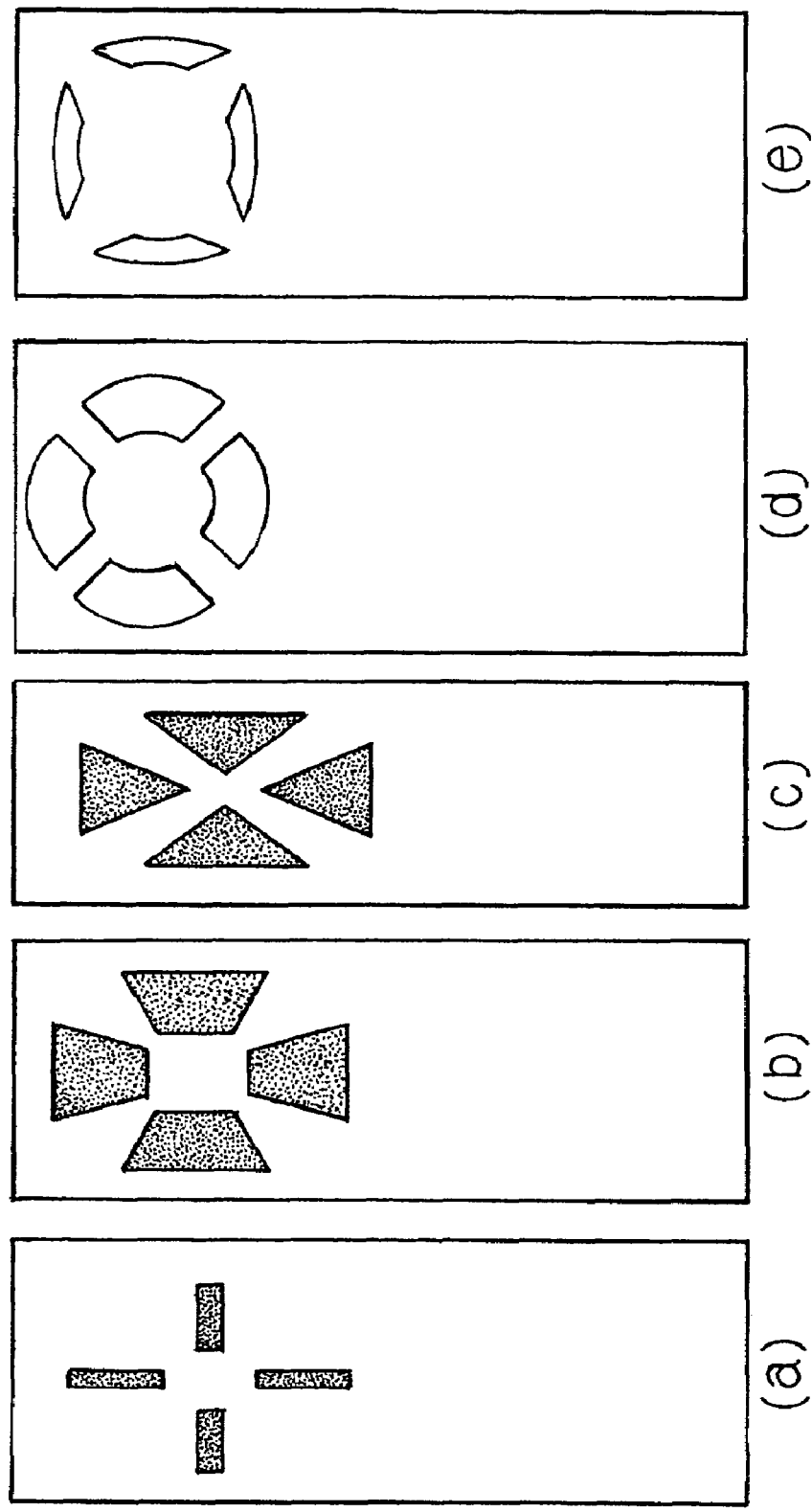

FIGS. 22(a-e) shows a number of electrode shape configurations that may prevent unnecessary shorting of currents in the epidural space, or help direct energy into certain patterns. FIG. 22(a) has greater efficiency since the electrodes are relatively far from each other. FIGS. 22(b and c) depict electrodes having relatively larger surface areas, thereby reducing resistance and allowing for higher currents. FIG. 22(d) has four electrodes farther apart forming a ring. FIG. 22(e) depicts relatively smaller electrodes that are further apart from each other to increase efficiency and minimize shunting of current between the electrodes.

FIG. 23 illustrates a similar concept but with 6 electrodes in a ring pattern to provide greater control of the direction of the electric field. Here, up to five or more anodal voltage levels may be used (if one is most cathodal), or up to six cathodal voltage levels may be used (if there is one distant anode, say, on a power source case). Those skilled in the art will appreciate that even other electrode configurations can be used together with more simultaneous pulses or varying amplitudes. Delivery of subthreshold pulses at various times may result in a two-dimensional locus of superactivation.

FIG. 24 shows the initial cross-pattern of five electrodes C1-C5 with some outer electrodes C6-C9. If any of the ring of electrodes C2-C5 is made a cathode, electrode C1 may be turned off and one or more outer electrodes C6-C9 can be made anodal to help maintain the field of excitation bounded on that side. FIG. 25 is yet another embodiment having five or more electrodes in an outer ring that could be anodal to contain the electric field toward the center.

Advantageously, these 2-dimensional configurations may be used to create suprathreshold potential areas as discussed above. Stimulation may be provided using a two-dimensional array of electrodes and configuring a range of anode/cathode relationships from the array. Moreover, simultaneous pulsing may be achieved by applying pulses of varying amplitudes to a selected group of cathodes in the array.

The advantages of the invention described herein can be generalized to applications for exciting any electrically excitable tissue within any organism, in addition to such tissue within a spine. Particularly, the same techniques of the present invention could be used for intraspinal, cortical, deep brain, peripheral nerve, heart or other muscle or organ stimulation as well. Further, the fields to be generated might have either constant current or constant voltage sources. Moreover, the invention can be generalized to using more than two cathodal electrodes to generate more than two subthreshold areas to be superposed in generating the suprathreshold potential area. Accordingly, the forgoing description is by way of example only and is not intended to be limiting. The invention is limited only as defined in the following claims and equivalents thereof.

We claim:

1. An apparatus for inducing action potentials at an adjustable locus of electrically excitable tissue of an organism, comprising in combination:
   (A) a plurality of electrodes forming an array adapted to be implanted adjacent to the tissue, the array having a first group of electrodes and a second group of electrodes, the second group of electrodes located at an outer position relative to the first group of electrodes;
   (B) at least one return electrode capable of being disposed within the organism;
   (C) a first set of at least one electrode of the first group of electrodes capable of being driven with a first pulse, the first pulse having a pulse parameter to generate a first subthreshold potential area in the tissue;
   (D) a second set of at least one electrode of the second group of electrodes capable of being driven with a second pulse, the second pulse having a pulse parameter to generate a second subthreshold potential in the tissue;
   (E) a generator configured to provide the first and second pulses between the return electrode and the first and second sets to cause a steerable electric field; and
   wherein a superposition of the first subthreshold potential area with the second subthreshold potential area results in a suprathreshold potential area of the adjustable locus where the action potentials are induced.

2. The apparatus of claim 1, wherein the first group of electrodes forms an inner ring of electrodes and the second group of electrodes forms an outer ring of electrodes.

3. The apparatus of claim 2, wherein the first group of electrodes that forms the inner ring are more cathodal with respect to the second group of electrodes that forms the outer ring thereby causing the steerable electric field to be contained within a certain region and causing outer tissue to be shielded from activation.

4. The apparatus of claim 1, wherein the apparatus further comprises in combination a metallic case, the metal case holding the generator and serving as the return electrode.

5. The apparatus of claim 1, wherein the first pulse and the second pulse are simultaneous in time.

6. The apparatus of claim 1, wherein the first pulse and second pulse are current pluses.

7. The apparatus of claim 1, wherein the first pulse and second pulse are voltage pulses.

8. The apparatus of claim 1, wherein the corresponding pulse parameter is selected from the group consisting of pulse width, pulse amplitude, pulse frequency, pulse rise time, pulse fall time, and pulse shape.

9. The apparatus of claim 1, wherein the generator is configured to increase pulse width, and wherein an increase of a first pulse width results in an increase of the first subthreshold area and an increase of the suprathreshold area toward the second set of electrodes.

10. An apparatus for inducing action potentials at an adjustable locus of electrically excitable tissue of an organism, comprising in combination:
    (A) a plurality of electrodes forming a two dimensional array adapted to be implanted adjacent to the tissue, the two dimensional array having a first group of electrodes and a second group of electrodes, the second group of electrodes being located at a more lateral position relative to the first group of electrodes;
    (B) at least one return electrode capable of being disposed within the organism;
    (C) a first set of at least one electrode of the first group of electrodes capable of being driven with a first pulse, the first pulse having a pulse parameter to generate a first subthreshold potential area in the tissue;
    (D) a second set of at least one electrode of the second group of electrodes capable of being driven with a second pulse, the second pulse having a pulse parameter to generate a second subthreshold potential in the tissue;
    (E) a generator configured to provide the first and second pulses between the return electrode and the first and second sets to cause a steerable electric field; and
    wherein a superposition of the first subthreshold potential area with the second subthreshold potential area results in a suprathreshold potential area of the adjustable locus where the action potentials are induced.

11. The apparatus of claim 10, wherein the apparatus further comprises in combination a metallic case, the metal case holding the generator and serving as the at least one return electrode.

12. The apparatus of claim 10, wherein the first pulse and the second pulse are simultaneous in time.

13. The apparatus of claim 10, wherein the first pulse and second pulse are current pluses.

14. The apparatus of claim 10, wherein the first pulse and second pulse are voltage pulses.

15. The apparatus of claim 10, wherein the corresponding pulse parameter is selected from the group consisting of pulse width, pulse amplitude, pulse frequency, pulse rise time, pulse fall time, and pulse shape.

16. The apparatus of claim 10, wherein the generator is configured to increase pulse width, and wherein an increase of a first pulse width results in an increase of the first subthreshold area and an increase of the suprathreshold area toward the second set of electrodes.

17. An apparatus for inducing action potentials at an adjustable locus of electrically excitable tissue of an organism, comprising in combination:
    (A) a plurality of electrodes forming an array adapted to be implanted adjacent to the tissue, the array having a first group of electrodes and a second group of electrodes, the first group of electrodes in an inner ring formation, the second group of electrodes in an outer ring formation;
    (B) at least one return electrode capable of being disposed within the organism;
    (C) at least one electrode of the first group of electrodes capable of being driven with a first pulse, the first pulse having a first pulse width to generate a first subthreshold potential area in the tissue;
    (D) at least one electrode of the second group of electrodes capable of being driven with a second pulse, the second pulse having a second pulse width to generate a second subthreshold potential in the tissue;
    (E) a generator configured to provide the first and second pulses between the return electrode and the at least one electrode of the first group and the at least one electrode of the second group to cause a steerable electric field; and
    wherein a superposition of the first subthreshold potential area with the second subthreshold potential area results in a suprathreshold potential area of the adjustable locus where the action potentials are induced.

18. The apparatus of claim 17, wherein the first pulse and the second pulse are simultaneous in time.

19. The apparatus of claim 17, wherein the generator is configured to increase pulse width, and wherein an increase of a first pulse width results in an increase of the first subthreshold area and an increase of the suprathreshold area toward the second group of electrodes.

* * * * *

UNITED STATES PATENT AND TRADEMARK OFFICE
CERTIFICATE OF CORRECTION

PATENT NO. : 7,657,318 B2  Page 1 of 1
APPLICATION NO. : 11/273310
DATED : February 2, 2010
INVENTOR(S) : King et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1115 days.

Signed and Sealed this

Thirtieth Day of November, 2010

David J. Kappos
*Director of the United States Patent and Trademark Office*